United States Patent
den Hoed

(10) Patent No.: US 9,149,512 B2
(45) Date of Patent: Oct. 6, 2015

(54) COLLAGEN MIXTURE AND METHOD OF MAKING THE SAME

(71) Applicant: Molecular Biology International, Inc., Sioux Center, IA (US)

(72) Inventor: Robert den Hoed, Sioux Center, IA (US)

(73) Assignee: Molecular Biology International, Inc., Sioux Center, IA (US)

(*) Notice: Subject to any disclaimer, the term of this patent is extended or adjusted under 35 U.S.C. 154(b) by 0 days.

(21) Appl. No.: 14/641,973

(22) Filed: Mar. 9, 2015

(65) Prior Publication Data

US 2015/0182598 A1    Jul. 2, 2015

Related U.S. Application Data

(60) Continuation of application No. 13/848,389, filed on Mar. 21, 2013, which is a continuation-in-part of application No. 13/562,680, filed on Jul. 31, 2012, which is a division of application No. 13/197,318, filed on Aug. 3, 2011, now Pat. No. 8,344,106, application No. 14/641,973, which is a continuation of application No. 13/751,741, filed on Jan. 28, 2013, which is a continuation-in-part of application No. 13/562,653, filed on Jul. 31, 2012, now Pat. No. 8,470,975, which is a division of application No. 13/197,318, filed on Aug. 3, 2011, now Pat. No. 8,344,106.

(51) Int. Cl.
*A61K 38/39*     (2006.01)
*C12P 21/06*     (2006.01)

(52) U.S. Cl.
CPC ............... *A61K 38/39* (2013.01); *C12P 21/06* (2013.01); *C12Y 302/01017* (2013.01)

(58) Field of Classification Search
None
See application file for complete search history.

(56) References Cited

U.S. PATENT DOCUMENTS

| | | | |
|---|---|---|---|
| 6,025,327 A * | 2/2000 | Alkayali | 514/17.2 |
| 6,780,841 B2 * | 8/2004 | Ishaq | 514/17.2 |
| 2008/0234195 A1 * | 9/2008 | Long et al. | 514/12 |

* cited by examiner

*Primary Examiner* — Suzanne M Noakes
(74) *Attorney, Agent, or Firm* — Zarley Law Firm, P.L.C.

(57) ABSTRACT

A collagen mixture having a portion of unhydrolyzed eggshell membrane collagen and Avian collagen.

11 Claims, 4 Drawing Sheets

COLLAGEN MIXTURE AND METHOD OF MAKING THE SAME

CROSS REFERENCE TO A RELATED APPLICATION

This application is a continuation of U.S. patent application Ser. No. 13/848,389 filed Mar. 21, 2013, which is a continuation-in-part of U.S. patent application Ser. No. 13/562,680 filed Jul. 31, 2012 which is a division of U.S. patent application Ser. No. 13/197,318 filed Aug. 3, 2011 and issued as U.S. Pat. No. 8,344,106 on Jan. 1, 2013. This application is also a continuation of U.S. patent application Ser. No. 13/751,741 filed Jan. 28, 2013, which is a continuation-in-part of U.S. patent application Ser. No. 13/562,653 filed Jul. 31, 2012 and issued as U.S. Pat. No. 8,470,975 on Jun. 25, 2013, which is a division of U.S. patent application Ser. No. 13/197,318 filed Aug. 3, 2011 and issued as U.S. Pat. No. 8,344,106 on Jan. 1, 2013.

BACKGROUND OF THE INVENTION

This invention is directed to creating a collagen mixture and more specifically, without limitation, creating a collagen mixture of unhydrolyzed eggshell membrane with LOS with Avian collagen.

Methods for producing collagen are known in the art. Such collagen is used for many things such as the healing of wounds, the production of skin creams and shampoo, the treatment of osteoarthritis and osteoporosis, and as an additive for human and pet food. While useful, the process is expensive, complicated, involving many steps, and requires harsh chemicals and inorganics which can damage unique properties. Accordingly, a method and mixture is needed in the art that addresses these deficiencies.

An objective of the present invention is to combine Type I, V, and X collagen with Type II collagen.

Another objective of the present invention is to provide a method of making unhydrolyzed eggshell membrane collagen with LOS that involves fewer steps and is unde-natured.

A still further objective of the present invention is to provide a method of producing Avian collagen Type II with a greater molecular weight.

These and other objectives will be apparent to one of ordinary skill in the art based upon the following written description, drawings, and claims.

SUMMARY OF THE INVENTION

A collagen mixture includes a portion of unhydrolyzed eggshell membrane collagen and a portion of Avian collagen. The method of making the eggshell membrane collagen includes separating a membrane from an eggshell, drying the membrane, and pulverizing the membrane into a powder. The method of making the Avian collagen includes adding an enzyme mixture to a thawed Avian cartilage to break the cartilage down into liquid form, heating the liquid cartilage to form a layer of liquid digest, raising the pH level of the liquid digest, heating the raised pH level liquid digest to form a partial solid content, and spray drying the partial solid content.

DETAILED DESCRIPTION OF THE PREFERRED EMBODIMENT

Figure 1:
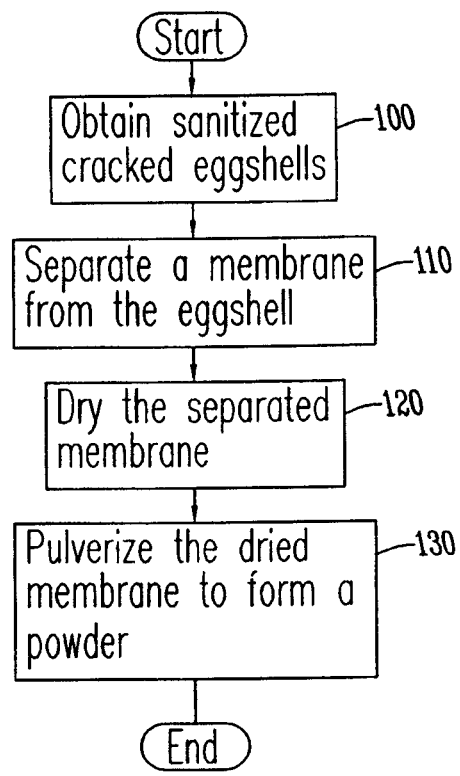
FIG. 1 is a flow diagram of a method for making unhydrolyzed eggshell membrane collagen.
Figure 2:
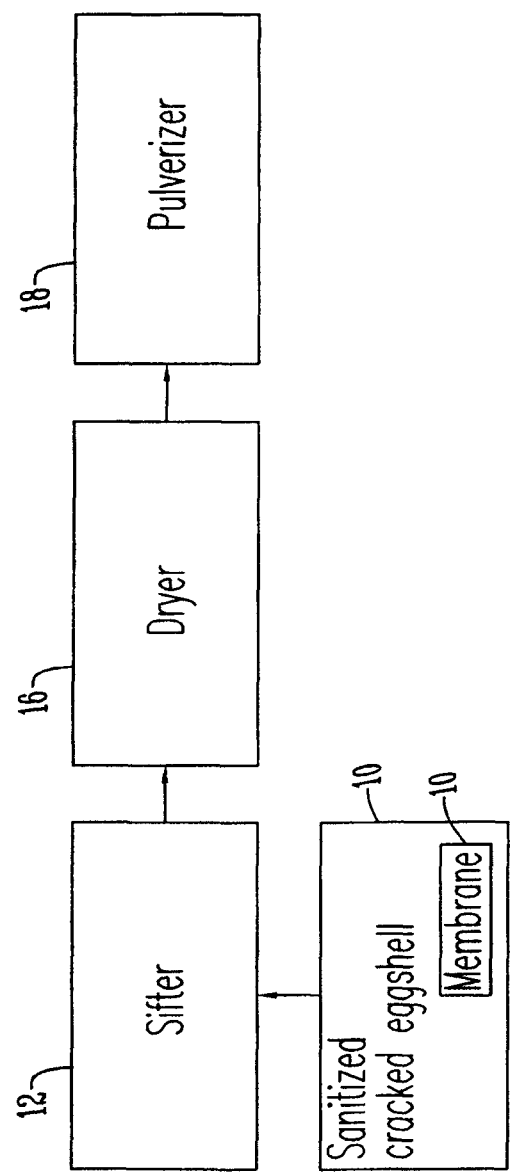
FIG. 2 is a schematic diagram of the environment for making unhydrolyzed eggshell membrane collagen.
Figure 3:
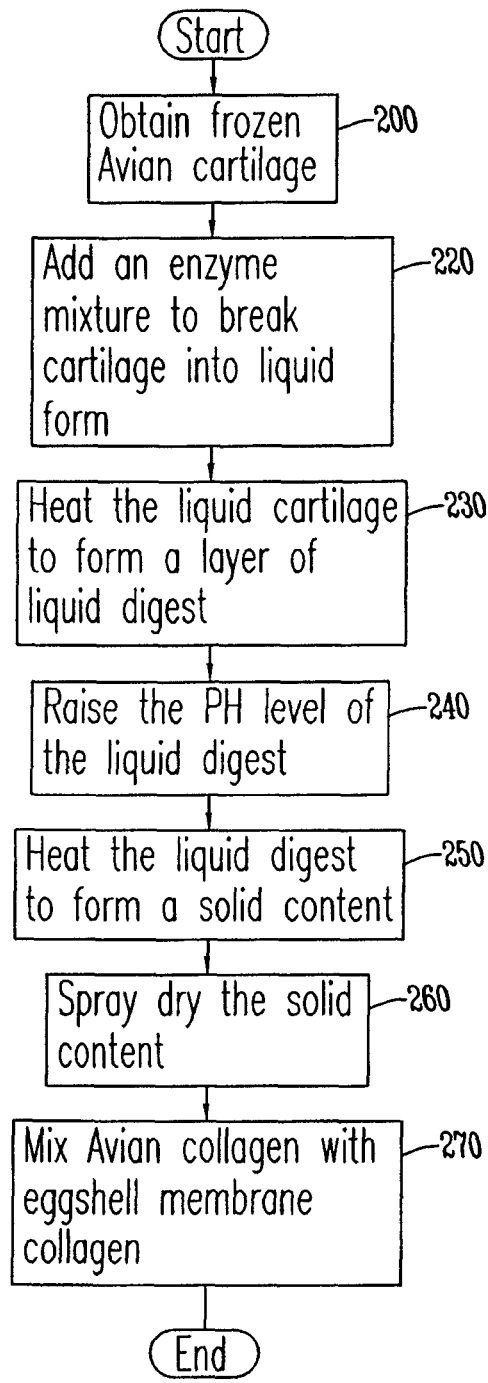
FIG. 3 is a flow diagram for a method of making a collagen mixture.
Figure 4:
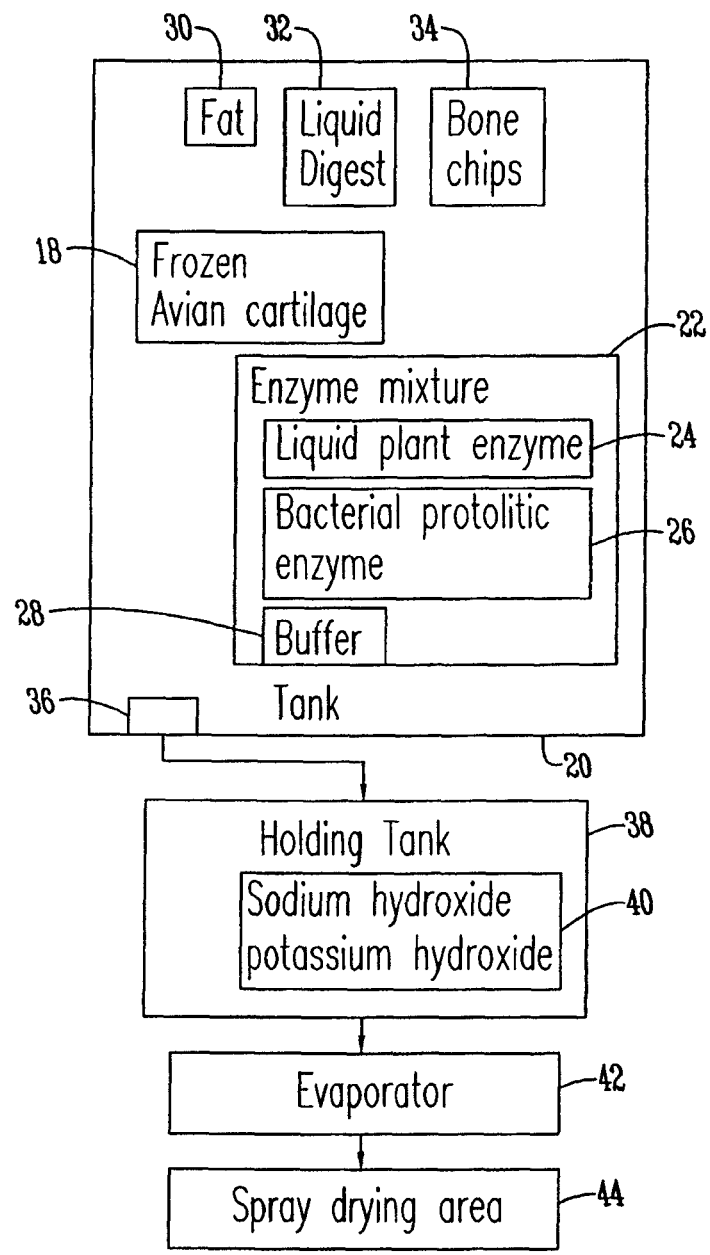
FIG. 4 is a schematic diagram of the environment for making a collagen mixture.

Referring to the Figures, the process of making unhydrolyzed eggshell membrane collagen containing Type I, V, and X collagen and lysosyme, ovatransferin, and sialic acid (LOS) begins at step 100 by obtaining sanitized cracked eggshells 10. The cracked eggshells 10 are placed on a sifter 12 at step 110 where the membrane 14 of the eggshell 10 is separated from the shell 10. The sifter 12 is of any type and preferably includes a fine mesh through which the shell 10 falls while the membrane 14 is transported to the end of the sifter 12.

Once separated, the membrane 14 is placed in a hot dryer 16 to dry the membrane and kill bacteria at step 120. While the dryer 16 is of any type, a motion dryer is preferred to facilitate faster drying. Once dried, the membrane 14, which is in flake form, is pulverized into a powder at step 130. Once in powder form, the membrane is packaged preferably in a fiber drum or bag for further use and/or processing.

The process of making the Avian collagen with LOS begins by obtaining Avian cartilage 18, typically in frozen form at step 200. At step 210, the frozen cartilage 18 is thawed by placing the cartilage in a tank 20 containing hot water. Once thawed, an enzyme mixture 22 is added to the thawed cartilage 18 which breaks the cartilage down into liquid form at step 220. Preferably, the enzyme mixture 22 includes a liquid plant derived enzyme 24 such as papain, ficen, or bromalain; a bacterial proteolytic enzyme 26, such as acid, neutral, or alkelian; and a buffer 28 such as acetic acid or sodium hydroxide and water for a pH buffering range of 4.8 to 6.8. As the enzyme mixture 22 breaks down the cartilage 18, the tank is heated to preferably 140°-160° F. such that the cartilage 18 separates into a top layer of fat 30, a middle layer of liquid digest 32, and a bottom layer of bone chips 34.

Once separated, at step 230, the bone chips 34 are swept away from a valve 36 in the bottom of the tank 20 and the liquid digest 32 is pumped through the valve 36 to a holding tank 38. Once pumped, at step 240, the pH level of the liquid digest 32 is raised by adding sodium hydroxide or potassium hydroxide 40 to the liquid digest 32 in the holding tank 38. Preferably the pH level of the liquid digest 32 is raised to a level of 5 to 11.

At step 250, after the pH level is raised, the liquid digest 32 is pumped into an evaporator 42 where the liquid digest 32 is heated to a solid content of between 10% to 75% such that the liquid has a syrup consistency. Preferably the liquid digest is heated at a temperature of 190°-230° F. to create a solid content of 15-40%.

Next, at step 260, the solid liquid digest 32 is transported to an area for spray drying 44. Preferably, the solid liquid digest is spray dried using high pressure pulse combustion. Also, a carrier such as multrodextrine is added to assist in pulling off extra water from the liquid digest 32. This results in a dry powder comprised of Avian collagen.

Once the Avian collagen has been spray dried it is mixed with the unhydrolyzed eggshell membrane collagen at step 270 to create a blended collagen mixture that includes Type I, II, III, IV, V and X collagen and LOS. Preferably the mixture has 70% Avian collagen to 30% eggshell membrane or alternatively 30% Avian collagen to 70% eggshell membrane collagen. Once combined, at step 280, the mixture is packaged and distributed.

The mixture of a portion of unhydrolyzed eggshell membrane and a portion of Avian collagen includes a minimum of 15 percent mucopolysacaride, a minimum of 5 percent chondroitin sulfite, a minimum of 2 percent hyaluronic acid, and a minimum of 20 percent protein. The following is a test result on the collagen mixture:

| Analyte | Result |
| --- | --- |
| chondroitin sulfate | 24.60% wt |
| hyaluronic acid | 11.96% wt |
| mucopolysacaride | 43.72% wt |

Alternatively, the collagen includes a minimum of 2 percent mucopolysacaride, a minimum of 0.1 percent of chondroitin sulfate, a minimum of 0.5 percent of hyaluronic acid, a minimum of 0.3 percent of glucosamine, and a minimum of 22 percent protein. The following is a test completed on the collagen:

| Analyste | Result |
| --- | --- |
| chondroitin sulfate | 0.406% wt |
| hyaluronic acid | 1.225% wt |
| mucopolysacaride | 9.075% wt |
| Glucosamine | 0.722% wt |

Accordingly, a collagen mixture and method of making the same has been disclosed that, at the very least, meets all the stated objectives.

What is claimed is:

1. A method of making a collagen mixture, comprising the steps of:
    obtaining a portion of unhydrolyzed eggshell membrane collagen in dry powder form and a portion of avian collagen; and
    combining the portion of unhydrolyzed eggshell membrane collagen and the avian collagen to form a combined portion that includes type III collagen.

2. The method of claim 1 wherein the combined portion includes type I, II, IV, V, and X collagen, and lysozyme, ovatransferin, and sialic acid (LOS).

3. The method of claim 1 wherein the combined portion comprises a minimum of 15 percent mucopolysaccharide, a minimum of 5 percent chondroitin sulfate, and a minimum of 2 percent hyaluronic acid.

4. The method of claim 3 wherein the combined portion comprises a minimum of 20 percent protein.

5. The method of claim 1 wherein the combined portion comprises a minimum of 2 percent mucopolysaccharide, a minimum of 0.1 percent chondroitin sulfate, and a minimum of 0.5 percent hyaluronic acid.

6. The method of claim 5 wherein the combined portion comprises a minimum of 2 percent protein.

7. The method of claim 5 wherein the combined portion comprises a minimum of 0.3 percent glucosamine.

8. The method of claim 1 further comprising the step of adding an enzyme to avian cartilage to produce the portion of avian collagen.

9. The method of claim 8 wherein the enzyme includes a liquid plant derived enzyme.

10. The method of claim 8 wherein the enzyme includes a plant derived proteolytic enzyme.

11. The method of claim 8 wherein the enzyme includes a plant derived proteolytic enzyme, a bacterial enzyme, and a buffer.

* * * * *